United States Patent [19]
Benoit et al.

[11] Patent Number: 5,262,438
[45] Date of Patent: Nov. 16, 1993

[54] PYRETHRINOID ESTERS OF 4-AMINO-2,3,5,6-TETRAFLUOROBENZYL ALCOHOL

[75] Inventors: Marc Benoit, Roquevaire; Jacques Demassey, Montevrain; Jean-Pierre Demoute, Neuilly Plaisance, all of France

[73] Assignee: Roussel-UCLAF, France

[21] Appl. No.: 906,406

[22] Filed: Jul. 1, 1992

[30] Foreign Application Priority Data

Jul. 4, 1991 [FR] France ................. 91 08378

[51] Int. Cl.$^5$ .................. A01N 53/00; C07C 69/74
[52] U.S. Cl. ...................... 514/531; 560/124
[58] Field of Search .............. 560/124; 514/531

[56] References Cited

U.S. PATENT DOCUMENTS

| | | |
|---|---|---|
| 4,024,163 | 5/1977 | Elliott .................. 560/124 |
| 4,370,346 | 1/1983 | Punja .................. 560/124 |
| 4,385,070 | 5/1983 | Bentley ................. 560/124 |
| 4,405,640 | 9/1983 | Punja .................. 560/124 |
| 4,429,153 | 1/1984 | Punja .................. 560/124 |
| 4,489,093 | 12/1984 | Martel ................. 560/124 |
| 4,732,903 | 3/1988 | Martel ................. 560/124 |
| 4,820,735 | 4/1989 | Naumann ............ 560/124 |
| 4,833,163 | 5/1989 | Martel ................. 560/124 |
| 4,939,172 | 7/1990 | Cadiergue ............ 560/124 |

FOREIGN PATENT DOCUMENTS 2066810 7/1981 United Kingdom ......... 560/124
2097384 11/1982 United Kingdom ......... 560/124

*Primary Examiner*—Michael L. Shippen
*Attorney, Agent, or Firm*—Bierman and Muserlian

[57] ABSTRACT

All possible stereoisomers and mixtures thereof of a compound of the formula

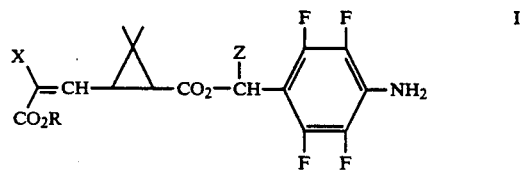

wherein X is selected from the group consisting of hydrogen, fluorine, chlorine and bromine, R is selected from the group consisting of optionally substituted alkyl, alkenyl, alkynyl and cycloalkyl of up to 8 carbon atoms, optionally substituted aryl and aralkyl of up to 14 carbon atoms and optionally substituted heterocyclic and Z is selected from the group consisting of hydrogen, methyl, —CN and —C≡CH having pesticidal, particularly insecticidal properties.

16 Claims, No Drawings

PYRETHRINOID ESTERS OF 4-AMINO-2,3,5,6-TETRAFLUOROBENZYL ALCOHOL

OBJECTS OF THE INVENTION

It is an object of the invention to provide the novel compounds of formula I and a process for their preparation.

It is another object of the invention to provide novel pesticidal compositions and a method of combatting pests.

These and other objects and advantages of the invention will become obvious from the following detailed description.

THE INVENTION

The novel compounds of the invention are all the possible stereoisomers and mixtures thereof of a compound of the formula

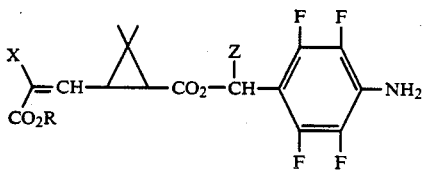

wherein X is selected from the group consisting of hydrogen, fluorine, chlorine and bromine, R is selected from the group consisting of optionally substituted alkyl, alkenyl, alkynyl and cycloalkyl of up to 8 carbon atoms, optionally substituted aryl and aralkyl of up to 14 carbon atoms and optionally substituted heterocyclic and Z is selected from the group consisting of hydrogen, methyl, —CN and —C≡CH.

Examples of R as alkyl are methyl, ethyl, propyl, isopropyl, butyl, sec-butyl, isobutyl, pentyl, hexyl, tert-butyl, tert-pentyl or neopentyl and examples of R as cycloalkyl are cyclopropyl, cyclobutyl, cyclopentyl and cyclohexyl optionally substituted with alkyl whose bond with the -COO group is on any one of its vertices such as 1-methylcyclobutyl, 1-methylcyclopentyl, 1-methylcyclohexyl and 2,2,3,3-tetramethylcyclopropyl.

Examples of R as alkenyl are vinyl, ethylene or 1,1-dimethylallyl and examples of R as alkynyl are ethynyl or propynyl. Examples of substituted alkyl are methyl, ethyl, propyl, isopropyl, butyl, isobutyl or tert.-butyl substituted with at least one functional group such as halogen, —OR', —SR', —NO$_2$,

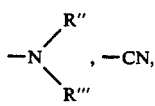

—SO$_3$H, —PO$_4$H$_2$, —COAlk$_1$, —SO$_2$Alk$_2$ or —SO$_3$Alk$_3$, R'' and R''' are individually hydrogen or alkyl of 1 to 8 carbon atoms and Alk$_1$, Alk$_2$ and Alk$_3$ are individually alkyl of 1 to 18 carbon atoms.

R may also be alkyl substituted by aryl such as benzyl or phenethyl optionally substituted by at least one member of the group consisting of —OH, —OAlk, Alk, —CF$_3$, —OCF$_3$, —SCF$_3$ and

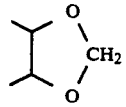

and Alk is alkyl of 1 to 8 carbon atoms. R may also be alkyl substituted on two adjacent carbon atoms by

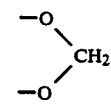

G$_1$ or substituted with

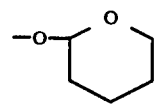

Examples of R substituted by at least one functional group are —(CH$_2$)$_n$—C(Hal)$_3$ in which n is an integer from 1 to 8 and Hal is halogen, for example —CH$_2$CCl$_3$, —CH$_2$CF$_3$, —CH$_2$—CH$_2$—CCl$_3$ or —CH$_2$—CH$_2$—CF$_3$, —(CH$_2$)$_{n1}$—CH(Hal)$_2$ in which Hal is defined as above and n$_1$ is a number from 0 to 8, for example —CH$_2$—CHCl$_2$, —CH$_2$—CHF$_2$ or —CHF$_2$; —(CH$_2$)$_n$—Hal in which n and Hal are defined as above, for example —CH$_2$—CH$_2$Cl or —CH$_2$—CH$_2$F; —C—(C(Hal)$_3$)$_3$ in which Hal is defined as above, for example —C(CF$_3$)$_3$ or

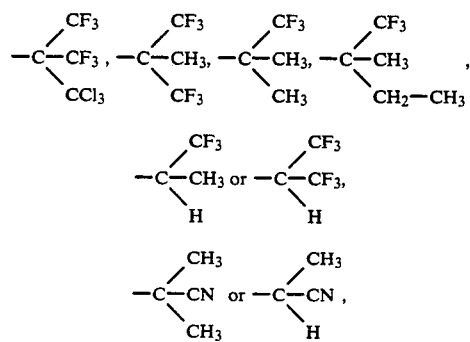

or —(CH$_2$)$_n$—CN, in which n is defined as previously;

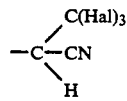

in which Hal is defined as previously, for example

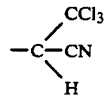

—(CH$_2$)$_n$—OR', in which n is defined as previously and R' is hydrogen or alkyl of 1 to 8 carbon atoms, for example —CH$_2$—OCH$_3$', —CH$_2$—CH$_2$—O—CH$_3$', —CH$_2$—CH$_2$—O—CH$_2$—CH$_3$ or —CH$_2$—CH$_2$—OH,

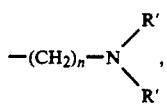

in which n and R' are defined as previously and the two R' can be different from each other, for example

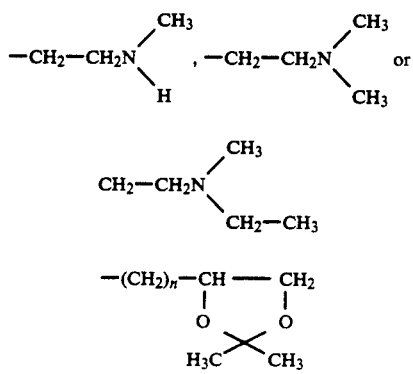

in which n is defined as previously, for example

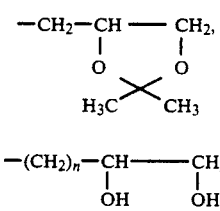

in which n is defined as previously, for example

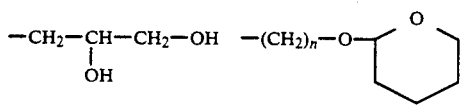

in which n is defined as previously, for example

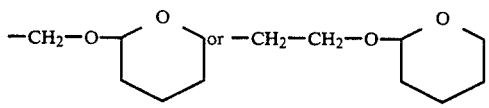

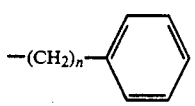

in which n is defined as previously, for example benzyl or phenethyl,

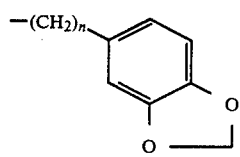

in which n is defined as previously, for example

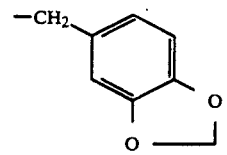

When R is an optionally substituted aryl, it is preferably phenyl or phenyl substituted by at least one OH, Oalk wherein alk is of 1 to 8 carbon atoms, or halogen or —$CF_3$, —$OCF_3$ or $SCF_3$.

When R is a heterocyclic, it is preferably pyridinyl, furanyl, thiophenyl, oxazolyl or thiazolyl.

Among the preferred compounds of formula I are those wherein X is fluorine, those wherein Z is hydrogen, or those in which R is alkyl of 1 to 4 carbon atoms, notably ethyl. Among the preferred compounds of the invention is the compound of Example 1.

The pesticidal compositions of the invention are comprised of a pesticidally effective amount of at least one compound of formula I and an inert carrier. The compositions may be in the form of powders, granules, suspensions, emulsions, solutions, aerosol solutions, combustible bands, baits or other known forms for these types of products.

The compositions generally contain a vehicle and/or a non-ionic surface-active agent to ensure a uniform dispersion of the mixture. Examples of vehicles are liquids such as water, alcohol, hydrocarbons and other organic solvents, mineral, animal and vegetable oils, powders such as talc, clay, silicates and kieselghur or a combustible solid.

The compositions are useful for combatting parasites, for example for combatting parasites of premises, parasites of vegetation and parasites of warm-blooded animals. Thus, the compositions of the invention can be used for combatting insects, nematodes and parasitic acaridae of vegetation and animals particularly for combatting parasites of premises, parasites of vegetation and parasites of warm-blooded animals.

The compositions can be used to combat insects in premises, notably to combat flies, mosquitoes and cockroaches and can also be used to combat insects in the agricultural domain, to combat for example, aphides, the larvae of lepidoptera and coleoptera, as well as to combat insects of the soil. They are used at doses of 10 g to 300 g of active ingredient per hectare.

The products of formula I are in addition photostable and are not toxic to mammals. All of these properties make the compositions of the invention products which correspond perfectly to the demands of the modern agrochemical industry, They allow crops to be protected while protecting the environment.

The compositions can also be used to combat parasitic acaridae and nematodes of vegetation and can also be used to combat parasitic acaridae of animals, for example ticks and notably ticks of the Boophilus species, those of the Hyalomnia species, those of the Amblyomnia species and those of the Rhipicephalus species or to combat all types of mites and notably the sarcoptic, psoroptic and chorioptic mite.

The insecticide compositions containing as active ingredient at least one of the products of formula I are particularly interesting.

The compositions are prepared according to the usual processes of the agrochemical industry or the veterinary industry or the industry for products intended for animal fodder. They may also contain additional pesticides.

The insecticide compositions of the invention preferably contain 0.005% to 10% by weight of active ingredient. According to an advantageous method, for use in premises, the compositions according to the invention are used in the form of fumigant compositions. The compositions of the invention can then be advantageously constituted, for the non-active part, by a combustible insecticide coil, or also by an incombustible fibrous substrate. In the latter case, the fumigant after incorporation of the active material is placed on a heating apparatus such as an electric vaporizer.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder. The dose of active ingredient can then be 0.03% to 1% by weight. In the case where an incombustible fibrous support is used, the dose of active material can be 0.03% to 95% by weight.

The compositions of the invention for use in premises can also be obtained by preparing a sprayable oil based on the active ingredient, the oil impregnating the wick of a lamp and then being lit. The concentration of active ingredient incorporated in the oil is preferably 0.03 to 95% by weight.

The insecticide compositions of the invention, as acaricide and nematicide compositions, can optionally have added to them one or more other pesticide agents. The acaricide and nematicide compositions can be in the form of powders, granules, suspensions, emulsions or solutions.

For acaricide use, wettable powders for foliar spraying containing 1 to 80%, or liquids for foliar spraying containing 1 to 500 g/liter of active ingredient are preferably used. Powders for foliar dusting can also be used containing 0.05 to 3% of active ingredient.

For nematocide use, liquids for soil treatment are preferably used containing 300 to 500 g/liter of active ingredient. The acaricide and nematocide compositions of the invention are preferably used at doses between 1 and 100 g of active ingredient per hectare.

To enhance the biological activity of the compositions of the invention, they can contain standard synergists used in such a case such as 1-(2,5,8-trioxadodecyl)-2-propyl-4,5-methylenedioxybenzene (or piperonyl butoxide) or N-(2-ethyl-heptyl)-bicyclo-[2,2-1]-5-heptene-2,3-dicarboximide, or piperonyl-bis-2-(2'-n-butoxyethoxy)ethylacetal (or tropital).

The novel method of the invention for combatting pests comprises contacting the pests with a pesticidally effective amount of at least one compound of formula I. Due to the fact that the compounds of formula I have an excellent general tolerance, the products of formula I are useful for combatting diseases caused by ticks and mites in man and in animals. The products of the invention may be used to combat lice in a preventive or curative way and to combat mites.

The products of formula I can be administered externally by spraying, by shampooing, by bathing or painting-on. The products for veterinary use can also be administered by painting the backbone by the so-called "pour-on" method. The products of the invention can also be used as biocides or as growth regulators.

The pesticidal compositions of the invention may also contain besides the compounds of formula I at least one second pesticidal ingredient selected from the group consisting of pyrethrinoid esters such as the esters of allethrolone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3-phenoxybenzyl alcohol and of α-cyano-3-phenoxybenzyl alcohol with 2,2-dimethyl-3-(2,2-dichlorovinyl)-cyclopropanecarboxylic acids, by the esters of α-cyano-3-phenoxy-benzyl alcohol with 2,2-dimethyl-3-(2,2-dibromovinyl)-cyclopropane carboxylic acids, by the esters of 3-phenoxybenzyl alcohol with 2-para-chlorophenyl-2-isopropyl acetic acid, by the esters of allethrolone, of 3,4,5,6-tetrahydrophtalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" is fluorine, chlorine or bromine, it being understood that the compounds of formula I can exist in all their possible stereoisomer forms, as well as the acid and alcohol copulas of the above pyrethrinoid esters.

The process of the invention for the preparation of the compounds of formula I comprises reacting an acid of the formula

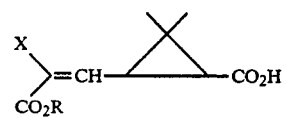

II or a functional derivative thereof wherein X and R have the above definitions with an alcohol of the formula

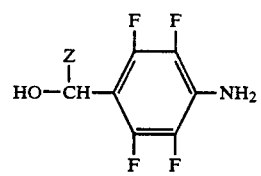

III or a functional derivative thereof wherein Z has the above definition to obtain the corresponding compound of formula I.

The compounds of formula II are known products described in the European patents No. 0,038,271; No. 0,041,021; No. 0,048,186 and No. 0,050,534. The compounds of formula III are compounds which are known generally and they can be prepared for example by the processes described in the Patent EP No. 31,199 and in ZH. Obshch Khim., Vol 37 (6), p. 1300-6 (1967).

In the following examples, there are described several preferred embodiments to illustrate the invention. However, it is to be understood that the invention is not intended to be limited to the specific embodiments.

EXAMPLE 1

2,3,5,6-tetrafluoro-4-amino-benzyl 1R[1α,3α, ΔE]-2,2-dimethyl-3-[3-ethoxy-2-fluoro-3-oxopropenyl]-cyclopropane carboxylate A solution of 1.05 g of dicyclohexylcarbodiimide, 60 mg of 4-dimethylamino-pyridine and 10 ml of methylene chloride was added at 5° C. to a mixture of 1 g of 4-amino-2,3,5,6-tetrafluorobenzyl alcohol [EP 31,199 or ZH Obshch Khim. Vol. 37 (6), p. 1300-6 (1967)], 40 ml of methylene chloride and 1.29 g of [1R[1α, 3α, Δ E]]-2,2-dimethyl-3-[3-ethoxy-2-fluoro-3-oxopropenyl]-cyclopropanecarboxylic acid (EP 0,050,534). The reaction mixture was stirred for 4 hours at 20° C. and then filtered and concentrated to obtain 2.5 g of a product which was chromatographed on silica. Elution with a hexane - ethyl acetate mixture (8-2) yielded 1.55 g of the desired product with a specific rotation of $[\alpha]_D=0$ (c=1% in $CHCl_3$).

EXAMPLE 2

2,3,5,6-tetrafluoro-4-amino-benzyl [1R[1α, 3α, ΔE]]-2,2-dimethyl-3-[3-tertbutyloxy-2-fluoro-3-oxopropenyl]-cyclopropane carboxylate Using the procedure of Example 1, 4-amino-2,3,5,6-tetrafluorobenzyl alcohol and [1R[1α, 3α,ΔE]]-2,2-dimethyl-3-[3-terbutyloxy-2-fluoro-3-oxopropenyl]-cyclopropane carboxylic acid were reacted to obtain the desired product melting at 104° C. and having a specific rotation of $[\alpha]_D=+11.5°\pm1°$ (c=0.95% in $CHCl_3$).

EXAMPLE 3

2,3,5,6-tetrafluoro-4-amino-benzyl [1R[1α, 3α, ΔZ]]-2,2-dimethyl-3-[3-(1,1,1,3,3,3-hexafluoro)-isopropoxy-3-oxopropenyl]-cyclopropane carboxylate Using the procedure of Example 1, 0.75 g of 4-amino-2,3,5,6-tetrafluoro-benzyl alcohol and 1.41 g of [1R[1α, 3α, ΔZ]-2,2-dimethyl-3-[3-(1,1,1,3,3,3-hexafluoro)-isopropoxy-3-oxopropenyl]-cyclopropane carboxylic acid were reacted to obtain 2.33 g of crude expected product which after chromatography yielded 1.1 g of the pure product.

NMR Spectrum 1.29 (s), 1.33 (s): $CH_3$; 2.02 (d), J=8.5: H cyclopropyl; 3.13 (m); $H_3$ cyclopropyl; 4.10 (wide s): $NH_2$; 5.13 (s): $CO_2$—$CH_2$; 5.80: CH—$(CF_3)_2$; 6.02 (d), J=11.5, 6.97 (dd), J=11 and 11.5: $H_2$ and $H_3$ of the propenyl.

EXAMPLE 4

A fumigant composition was obtained by homogeneously mixing the following ingredients:

| | |
|---|---|
| product of Example 1 | 0.25 g |
| Tabu powder | 25.00 g |
| cedar leaf powder | 40.00 g |
| pine sawdust | 33.75 g |
| brilliant green | 0.50 g |
| p-Nitrophenol | 0.50 g |

BIOLOGICAL STUDY

Study of the Knock-down Effect on the Housefly

The test insects were 4-days old female houseflies and the test was carried out by direct spraying at a concentration of 0.25 g/liter in a Kearns and March chamber using a mixture of acetone (5%) and Isopa L (petroleum solvent) as solvent (solvent used was 2 ml per second). 50 insects per treatment were used and checks were made every minute for 10 minutes, then after 15 minutes and the $KT_{50}$ was determined. The relative power of the product of Example 1 relative to bioallethrine was 7.65.

Various modifications of the compounds and method of the invention may be made without departing from the spirit or scope thereof and it is to be understood that the invention is intended to be limited only as defined in the appended claims.

What is claimed is:

1. All possible stereoisomers and mixtures thereof of a compound of the formula

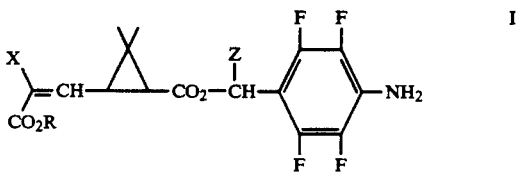

wherein X is selected from the group consisting of hydrogen, fluorine, chlorine and bromine, R is alkyl of up to 4 carbon atoms and Z is selected from the group consisting of hydrogen, methyl, —CN and C≡CH.

2. A compound of claim 1 wherein X is fluorine.
3. A compound of claim 1 wherein Z is hydrogen.
4. A compound of claim 1 wherein R is ethyl.
5. A compound of claim 1 which is [2,3,5,6-tetrafluoro-4-amino-benzyl] 1R(1α, 3α, ΔE)-2,2-dimethyl-3-[3-ethoxy-2-fluoro-3-oxo-propenyl]-cyclopropane carboxylate.
6. An insecticidal composition comprising an insecticidally effective amount of at least one compound of claim 1 and an inert carrier.
7. A composition of claim 6 wherein X is fluorine.
8. A composition of claim 6 wherein Z is hydrogen.
9. A composition of claim 6 wherein R is ethyl.
10. A composition of claim 6 wherein the active ingredient is [2,3,5,6-tetrafluoro-4-amino-benzyl] 1R(1α, 3α, ΔE)-2,2-dimethyl-3-[3-ethoxy-2-fluoro-3-oxo-propenyl]-cyclopropane carboxylate.
11. A compound of claim 6 also containing at least one member of the group consisting of esters of allethrolone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropane carboxylic acid, by the esters of 3-phenoxybenzyl alcohol and of α-cyano-3-phenoxybenzyl alcohol with 2,2-dimethyl-3-(2,2-dichlorovinyl)-cyclopropane carboxylic acid, by the esters of α-cyano-3-phenoxy-benzyl alcohol with 2,2-dimethyl-3-(2,2-dibromovinyl)-cyclopropane carboxylic acid, by the esters of 3-phenoxybenzyl alcohol with 2-parachlorophenyl-2-isopropyl acetic acid, by the esters of allethrolone, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" is fluorine, chlorine or bromine.

12. A method of combatting insects comprising contacting insects with an insecticidally effective amount of at least one compound of claim 1.

13. A method of claim 12 wherein X is fluorine.

14. A method of claim 12 wherein Z is hydrogen.

15. A method of claim 12 wherein R is ethyl.

16. A method of claim 12 wherein the active ingredient is [2,3,5,6-tetrafluoro-4-amino-benzyl] 1R(1α, 3α, ΔE)-2,2-dimethyl-3-[3-ethoxy-2-fluoro-3-oxo-propenyl]-cyclopropane carboxylate.

* * * * *